(12) United States Patent
Dennerlein

(10) Patent No.: US 8,861,823 B2
(45) Date of Patent: Oct. 14, 2014

(54) METHOD FOR RECONSTRUCTION OF A TWO-DIMENSIONAL SECTIONAL IMAGE CORRESPONDING TO A SECTIONAL PLANE THROUGH A RECORDED OBJECT AND X-RAY DEVICE

(75) Inventor: Frank Dennerlein, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 349 days.

(21) Appl. No.: 13/110,963

(22) Filed: May 19, 2011

(65) Prior Publication Data

US 2011/0286629 A1 Nov. 24, 2011

(30) Foreign Application Priority Data

May 20, 2010 (DE) .......................... 10 2010 029 187

(51) Int. Cl.
*G06K 9/00* (2006.01)
*G06T 11/00* (2006.01)
*A61B 6/00* (2006.01)

(52) U.S. Cl.
CPC ............. *G06T 11/006* (2013.01); *G06T 11/008* (2013.01); *A61B 6/5223* (2013.01); *G06T 2211/421* (2013.01)
USPC ............................ 382/131; 382/103; 382/132

(58) Field of Classification Search
None
See application file for complete search history.

(56) References Cited

U.S. PATENT DOCUMENTS 7,778,455 B2 * 8/2010 Araikum ....................... 382/131
2001/0038681 A1 * 11/2001 Stanton et al. ................... 378/55

OTHER PUBLICATIONS

NPL—Jiang Hsieh, Computed Tomography 2nd Edition (SPIE Press Monograph, vol. PM188. 2009, p. 55-117).*
NPL—Demirkaya et al., Image processing with MATLAB applications in medicine and biology (CRC Press, 2009, pp. 182-186).*
NPL—Jiang Hsieh, Computed Tomography 2nd Edition (SPIE Press Monograph, vol. PM188. 2009, p. 1-21 and 55-117).*
NPL—Jiang Hsieh, Computed Tomography 2nd Edition (SPIE Press Monograph, vol. PM188. 2009, Chapter 10 "multscan CT", pp. 375-432.*
Frank Dennerlein at al.; "A Factorization Approach for Cone-Beam Reconstruction on a Circular Short-Scan", IEEE Transactions on Medical Imaging, July 2008, pp. 887-896, vol. 27, No. 7.
Dennerlein et al., "Cone-beam Reconstruction on a Circular Short-Scan Using the Factorization Approach". Proceedings of the Fully3D, 2007, pp. 346-349.
Riabkov et al., Accelerated cone-beam backprojectin using GPU-CPU hardware. Proc. of the 9th International meeting on Fully Three-Dimensional Image Reconstruction in Radiology and Nuclear Medicine, 2007, pp. 68-71.
Hillebrand et al., "Interactive GPU-Accelerated Image Reconstruction in Cone-Beam CT", 2009, pp. 1-8.
Pack et al.; "Cone-Beam Reconstruction Using the Backprojection of Locally Filtered Projections"; IEEE Trans.Med.lmaging vol. 24, No. 1, Jan. 2005, pp. 70-85.
Dennerlein, "Image Reconstruction from Fan-Beam and Cone-Beam Projections", Technische Fakultät der Universität Erlangen-Nürnberg, 2008, pp. 1-139.

* cited by examiner

*Primary Examiner* — Wesley Tucker

(57) ABSTRACT

A method for reconstruction of a two-dimensional sectional image corresponding to a sectional plane through a recorded object from two-dimensional projection images recorded along a recording trajectory at different projection angles with an X-ray device is proposed. The sectional plane having at least two intersection points with the imaging trajectory is selected. After selection of the sectional plane, an intermediate function on the sectional plane is determined by backprojection of the projection images processed with a differentiation filter. The object densities forming the sectional image are determined from the intermediate function by a two-dimensional iterative deconvolution method.

11 Claims, 2 Drawing Sheets

METHOD FOR RECONSTRUCTION OF A TWO-DIMENSIONAL SECTIONAL IMAGE CORRESPONDING TO A SECTIONAL PLANE THROUGH A RECORDED OBJECT AND X-RAY DEVICE

CROSS REFERENCE TO RELATED APPLICATIONS

This application claims priority of German application No. 10 2010 029 187.0 filed May 20, 2010, which is incorporated by reference herein in its entirety.

FIELD OF THE INVENTION

The invention relates to a method for reconstruction of a two dimensional sectional image corresponding to a cross-section through a recorded object from two-dimensional project images recorded with an X-ray device along an imaging trajectory at different projection angles as well as to an X-ray device.

BACKGROUND OF THE INVENTION

The determination of three-dimensional datasets using two-dimensional projection images which describe an object to be presented from different projection angles is widely known. To do this an X-ray emitter of an X-ray device follows an imaging trajectory, for example a circular track, with the two-dimensional X-ray projection images being recorded at prespecified projection angles.

In X-ray devices allowing such three-dimensional imaging, especially CT devices, which are used for example for non-destructive material testing or medical angiography, the generated three-dimensional object datasets are often visualized not directly as a three-dimensional view but as two-dimensional sectional images. A sectional image shows the spatial object density of the object under examination on a sectional plane usually selected by the user. Thus for example precise quantitative length or density measurements are made possible. In neuro-radiology bleeding is often detected on sectional images and sectional image information is likewise often used for blood perfusion measurements. Such measurements are impossible or only possible to a limited extent in projection images or in the volumetric views synthesized from the three-dimensional object dataset.

To visualize sections through the object dataset, the object density function does not have to be known in the overall image volume but only on the selected sections. Thus in the article "Interactive GPU-accelerated image reconstruction in cone-beam CT" by Lars Hillebrand et al., Proceedings of the SPIE, Volume 7258 (2009), page 72582A, a method for CT reconstruction by means of filtered backprojection (FBP) is proposed, which computes the object density online shortly before the visualization only on the sectional planes for which the sectional images are to be displayed. No interpolation of the sectional image from a three-dimensional object dataset is thus necessary. The computation is very efficient and can thus deliver interactive updates of the display if the user modifies the sectional position (sectional plane) and/or at least one reconstruction parameter of the filtered backprojection.

In addition to the filtered backprojection, iterative reconstruction is also known as a reconstruction method, which has a number of advantages over filtered backprojection. Thus prior knowledge about the object can elegantly be introduced in iterative methods as an ancillary condition. This prior knowledge, for example about the possible density range of the object, the object extent or assumptions about object structures makes better image quality possible than with filtered backprojection methods.

According to the current prior art however the object density function must always be calculated in the overall image volume when iterative methods are used which despite modern computation hardware is very time-consuming and can thus not be undertaken interactively or in real time. The reconstruction of an individual section as in the above-mentioned article, is not possible.

SUMMARY OF THE INVENTION

The underlying object of the invention is thus to specify a method with which effectively and in a timely manner a high-quality two-dimensional sectional image can be obtained using an iterative method.

To achieve this object, in a method of the type mentioned at the start, the following inventive steps are provided:

Selection of the sectional plane having at least two intersection points with the recording trajectory, After selection of the sectional plane, determination of an intermediate function on the sectional plane by back-projection of the derived projection images and Determination of the object densities forming the sectional image through a two-dimensional iterative deconvolution method.

Thus first of all, as normally, the two-dimensional projection images are recorded in cone beam geometry along the imaging trajectory. In this case a smooth, closed curve can expediently be used, especially a circular track, as the imaging trajectory for recording the projection images.

If the user now wishes to display an image, he selects a sectional plane within the framework of the display process. The selection of the sectional plane is then restricted in the inventive method to such sectional planes as have at least two intersection points with the imaging trajectory. The reason for this requirement lies in the following steps as will be further explained below. Although the selection of available sectional planes is restricted by this method, this is more than compensated for by an efficient and timely determination of the sectional image, especially in real-time and a significantly improved quality in the inventive method. Determination in real time means that the user receives the first reconstructed image immediately after selecting the sectional plane.

After the sectional plane is selected the reconstruction is undertaken. Then (or also even beforehand since the derived projection images can naturally also be used for a number of sectional image reconstructions) the projection images are derived, this means especially processed with a differentiation filter, whereby finally any given differentiation filter is able to be used in relation to the recording trajectory parameters with a fixed beam direction. The images thus derived are then, after selection of the sectional plane in each case, back-projected onto the sectional plane to determine an intermediate function. This is only possible under the condition that at least two intersection points with the imaging trajectory are present. By contrast with a filtered backprojection, a local operation, namely a derivation, is thus used as a filter in order to obtain the intermediate function for different places in the sectional plane. A possible concrete procedure for obtaining this intermediate function is described in another context in the article entitled "A factorization approach for cone-beam reconstruction on a circular short-scan" by F. Dennerlein et al., IEEE Trans. Med. Imag., 27(7): 887-896, 2008.

However it is now known, cf. for example the article entitled "Cone-beam reconstruction using the backprojection of locally filtered projections" by J. D. Pack, F. Noo and R. Clackdoyle IEEE Trans. Med. Imag., 24(1):70-85, 2005 that the object density on a sectional plane by a two-dimensional convolution with a Hilbert-like kernel (where necessary also the Hilbert kernel itself) theoretically exactly correlates with the intermediate function on the section. Consequently an equation system to be solved is produced discretized if one wishes to determine the object density for different excels of the sectional image from the intermediate function.

Accordingly it is now proposed in accordance with the invention to use an iterative two-dimensional deconvolution method in order to obtain the object densities in the sectional plane and consequently the sectional image. In such cases the iteration method can especially advantageously take account of any given ancillary conditions about the object such as in classic iterative reconstruction. A possible iterative method is likewise described in the already cited article entitled "A factorization approach for cone-beam reconstruction on a circular short-scan" by F. Dennerlein et al., IEEE Trans. Med. Imag., 27(7):887-896, 2008. As an alternative to this article, the publication "Cone-beam reconstruction on a circular short-scan using the factorization approach" by F. Dennerlein et al., Proceedings of the Fully3D, pages 346-349, Lindau, Germany, 2007, can also be considered.

The method described allows sectional images of very high quality to be produced. Especially with the use of a circular track as the imaging trajectory, the sectional images can exhibit a significantly higher image quality than corresponding sectional images reconstructed with filtered backprojection, for example with a Feldkamp algorithm. The above-mentioned computation steps can be executed efficiently so that real-time computation of the object density directly before display is possible. With the classical iterative method this would not be possible simply because of the processing time.

The computation efficiency of the inventive method is especially a result of only one or a few sectional images having to be computed, not the complete three-dimensional image volume. Consequently a much greater computing efficiency results than with conventional iterative methods.

The real-time reconstruction at the time of visualization makes it possible to interactively modify reconstruction parameters or the prior knowledge described as an ancillary condition and immediately make the effects on the sectional image visible. There can thus the provision for a new determination of a sectional image to take place after a user-side modification of at least one reconstruction parameter of the backprojection and/or of the deconvolution method and/or of an ancillary condition of the deconvolution method. Interactive settings can must be changed and thus optimized by the user, who receives feedback immediately in order to obtain a sectional image adapted to his requirements.

A further advantage of the inventive method is that, by comparison with procedures which initially reconstruct a three-dimensional object dataset and then extract sectional images by means of interpolation, the disadvantageous interpolation is omitted since in the approach presented here the object density is determined directly on the sectional plane.

The reconstructed sectional images can be displayed on a display facility, for example on a monitor of the X-ray device.

In a further embodiment of the invention there can be provision for a number of sectional planes to be selected and for a sectional image to be determined for each sectional plane. It is thus conceivable to select a number of different sectional planes with at least two intersection points with the imaging trajectory, whereby in accordance with the inventive iterative method, the corresponding sectional image that shows the object density in this sectional plane can be efficiently determined for each of these planes in real time. In such cases it has proved to be especially advantageous that the individual reconstruction processes run independently of one another, so that in an especially expedient further embodiment of the inventive method there can be provision for the determination of the individual sectional images to be carried out in parallel, especially using a processing unit, especially a CPU or GPU, for each sectional image. The individual sectional images can thus be reconstructed in parallel to further reduce the processing times, especially by a CPU being made available for each reconstruction.

The at least one sectional plane will generally be selected by a user, for example by a corresponding user interface to the X-ray device or also to a processing device used. For example an abstract view or a preliminary scan of the object to select the sectional plane can be displayed, in which the user can mark or respectively select the at least one desired sectional plane. In this context it is especially useful if, for user-controlled selection of the sectional plane, first of all the set of all planes having at least two intersection points with the imaging trajectory is determined and the selection of the sectional plane is restricted to these planes. The sectional planes for which he can obtain high-quality sectional images through the advantageous inventive method are thus communicated to the user. Other sectional planes are then not able to be selected right from the start and can be displayed for example in red, while possible sectional planes are displayed in green.

In a further advantageous embodiment of the present invention there can be provision for sectional planes also having fewer than two intersection points with the imaging trajectory to be able to be selected, for which a sectional image is reconstructed using filtered backprojection. In this way coverage of all possible sectional planes is achieved, whereby whenever the proposed iterative method for creating high-quality sectional images is able to be used, this method is also used. As an alternative for the sectional planes which do not have to intersection points with the imaging trajectory, another method is always still then available to the user, for example the method based on filtered backprojection cited in the article by L. Hillebrand et al. mentioned at the start. The user should naturally be made aware in such cases of which method is being used to determine the sectional image. This can be done for example during the selection of the sections, by sectional planes having at least two intersection points with the imaging trajectory being displayed in one color, others in another color, or by a similar method.

In addition to the method, the invention also relates to an X-ray device comprising a control device embodied for carrying out the inventive method. All remarks relating to the method can be applied similarly to the inventive X-ray device. It should be pointed out that the method evaluating the projection images as raw data can also be executed on a computing device, for example at a diagnostic workstation.

BRIEF DESCRIPTION OF THE DRAWINGS

Further advantages and details of the present invention emerge from the exemplary embodiments described below as well as with reference to the drawing, in which.

DETAILED DESCRIPTION OF THE INVENTION

Figure 1:
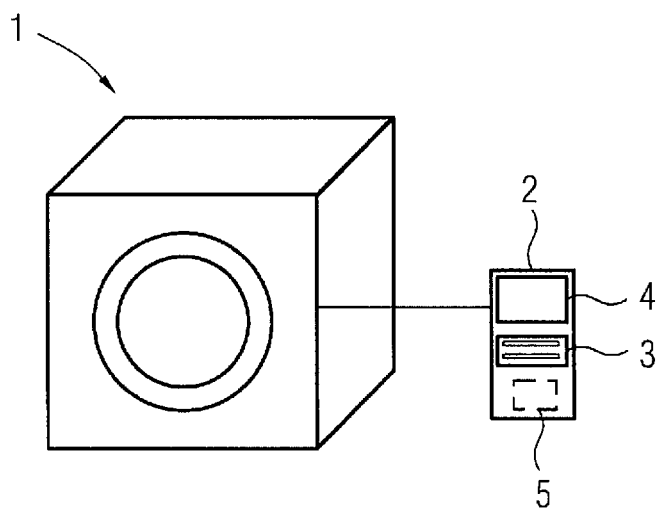
FIG. 1 shows an inventive X-ray device.

FIG. 1 shows an inventive X-ray device 1, here a CT device, which as generally known comprises an X-ray source able to be moved along an imaging trajectory and one or more X-ray detectors especially positioned opposite the X-ray source and moved along with it, which are not shown in any greater detail in the figure.

Furthermore an operating device 2 with an input facility 3 and a display facility 4 are provided, here a screen or monitor. The operation of the X-ray device 1 is controlled via a control device 5 which is embodied for executing the inventive method described below.

It should once again be pointed out at this juncture that other processing devices can also be embodied for editing projection data, i.e. measurement data, in sectional images to be displayed in accordance with the inventive method.

Figure 2:
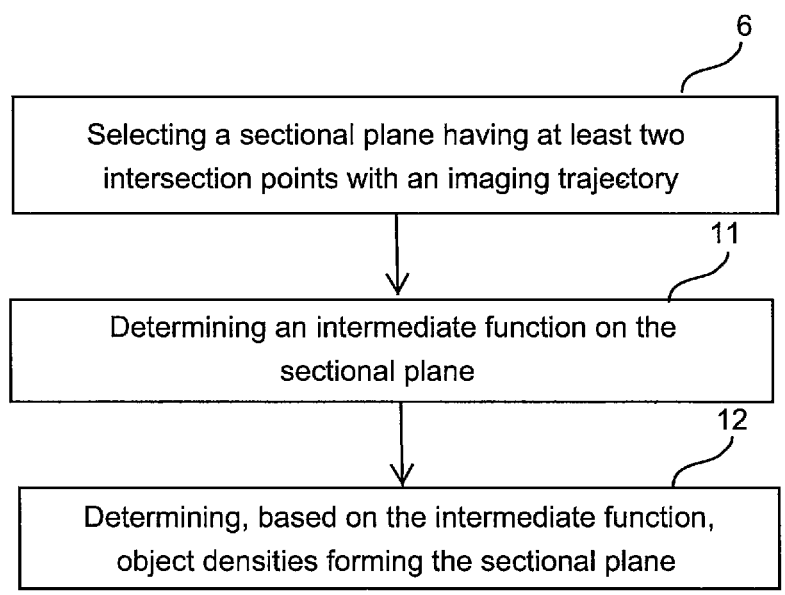
FIG. 2 shows a flowchart of the inventive method.
Figure 3:
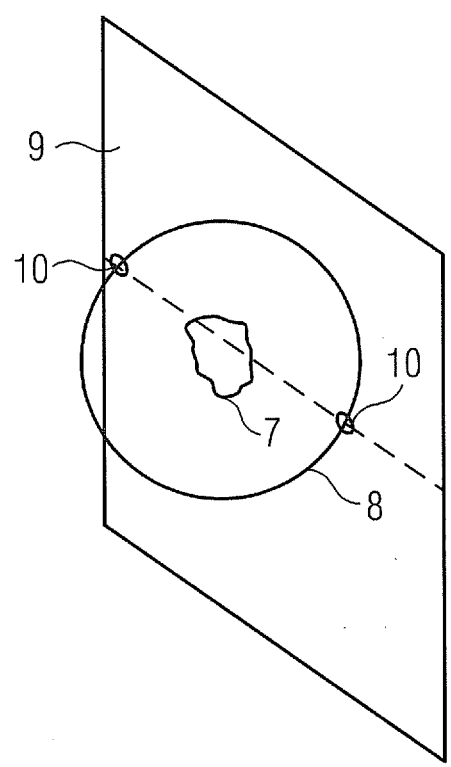
FIG. 3 shows a basic diagram for selecting the sectional plane.

FIG. 2 shows a flowchart of a form of embodiment of the inventive method. After two-dimensional projection images are recorded in cone beam geometry using a specific imaging trajectory, in this case a closed circular track, in a step 6 at least one sectional plane through the recorded object is defined by a user which has two intersection points with the imaging trajectory. This will be explained in greater detail with reference to FIG. 3 which shows an object 7 and the imaging trajectory 8 naming around it. In this figure a sectional plane has two intersection points 10 with the imaging trajectory 8.

In this exemplary embodiment there is provision for supporting the user in their choice in that, during the choice, not only an abstract or a representation of the object 7 originating from a preliminary scan is shown, but also a possible sectional plane 9 is shown which the user can then modify until it corresponds to his requirements. In this case a check is made as to whether the possible sectional plane has two intersection points with the imaging trajectory 8. If it does it is shown in green, otherwise in orange or red. It should be pointed out at this juncture that fewer than two intersection points with the sectional planes 9 forming the imaging trajectory 8 can be selected, which can then however the processed with the alternative algorithm not described in any greater detail here using filtered backprojection.

If one or more sectional planes with the least two intersection points with the imaging trajectory are now selected, in step 11a computation is started for each sectional plane which explicitly determines the object density forming the sectional image in pixels in the sectional plane using an iterative method. The processes are independent for all sectional planes, so that the sectional image is determined in parallel for each sectional plane, here using a CPU for each sectional image.

In step 11 in this case an intermediate function on the sectional plane is first defined. To do this the projection images derived with a differentiation filter are backprojected into the plane, as has already been explained in greater detail in the general description.

If the intermediate function is available for the sectional plane, in step 12 a two-dimensional iterative deconvolution method is used to determine the object density at different pixels from the intermediate function, since the relationship between the intermediate function and the object density is established by a Hillbert-like kernel.

In this case boundary conditions are used in step 12, which contain prior knowledge about the object and which—precisely like one or more reconstruction parameters—can likewise be selected by a user.

To conclude step 12, a sectional image is then obtained in real-time for each selected plane, which can then also be displayed directly, for example on the display facility 4.

It should also be pointed out that it is easy for the user, because of the fast and efficient determination of the sectional image or sectional images, to modify reconstruction parameters or boundary conditions respectively by way of the control device 2. If he does this, steps 11 and 12 are executed again and he obtains practically in real time a new sectional image and can immediately assess the effects of his modifications.

The invention claimed:

1. A method for reconstructing a two-dimensional sectional image corresponding to a sectional plane through a recorded object from two-dimensional projection images recorded along an imaging trajectory at different projection angles with an X-ray device, comprising:
   selecting a sectional plane, wherein the selecting comprises restricting the selected sectional plane to sectional planes having at least two intersection points with the imaging trajectory;
   processing the projection images with a differentiation filter;
   determining an intermediate function on the selected sectional plane by backprojecting the processed projection images onto the selected sectional plane; and
   determining object densities forming a sectional image from the intermediate function by a two-dimensional iterative deconvolution method,
   wherein a plurality of sectional planes is selected and a respective sectional image is determined for each sectional plane,
   wherein each sectional image is individually reconstructed based on a respective selected sectional plane independently from the other sectional planes.

2. The method as claimed in claim 1, wherein the imaging trajectory comprises a smooth and closed curve.

3. The method as claimed in claim 2, wherein the imaging trajectory is a circular track.

4. The method as claimed in claim 1, wherein the sectional image is determined again after a modification of at least one reconstruction parameter of the deconvolution method and/or of a boundary condition of the deconvolution method.

5. The method as claimed in claim 4, wherein the modification is made by a user.

6. The method as claimed in claim 1, wherein each respective sectional image is determined in parallel with each other using a processing unit for each sectional image.

7. The method as claimed in claim 6, wherein the processing unit comprises a CPU or GPU.

8. The method as claimed in claim 1, wherein the selection of the sectional plane is controlled by a user.

9. An X-ray device for reconstructing a two-dimensional sectional image corresponding to a sectional plane through a recorded object from two-dimensional projection images recorded along an imaging trajectory at different projection angles, comprising:
   an input device;
   a control device for:
      displaying a plurality of sectional planes, wherein sectional planes having at least two intersection points with the imaging trajectory are displayed and are distinguishable to a user from sectional planes not having at least two intersection points with the imaging trajectory;
      selecting a sectional plane from the plurality of the sectional planes, wherein the selecting comprises restricting the selected sectional plane to one of the sectional planes having the at least two intersection points with the imaging trajectory;
      processing the projection images with a differentiation filter;

determining an intermediate function on the sectional plane by backprojecting the processed projection images onto the selected sectional plane; and determining object densities forming a sectional image from the intermediate function by a two-dimensional iterative deconvolution method, wherein the sectional image is individually reconstructed based on the selected sectional plane independently from further sectional planes; and a display device.

10. A method for reconstructing a two-dimensional sectional image corresponding to a sectional plane through a recorded object from two-dimensional projection images recorded along an imaging trajectory at different projection angles with an X-ray device, comprising:

selecting a first sectional plane, wherein the selecting comprises restricting the selected sectional plane to a sectional plane having at least two intersection points with the imaging trajectory;

processing the projection images with a differentiation filter;

determining an intermediate function on the selected sectional plane by backprojecting the processed projection images onto the selected sectional plane;

determining object densities forming a sectional image from the intermediate function by a two-dimensional iterative deconvolution method, wherein a plurality of first sectional planes is selected and a respective sectional image is determined for each sectional plane, wherein each first sectional image is individually reconstructed based on a respective selected sectional plane independently from the other first sectional planes; and selecting a further sectional plane having fewer than two intersection points with the imaging trajectory, and wherein a reconstruction of the further selected sectional image is performed by a method comprising filtered backprojection.

11. The method of claim 1, further comprising displaying a plurality of sectional planes, wherein sectional planes having at least two intersection points with the imaging trajectory are displayed and are distinguishable to a user from sectional planes not having at least two intersection points with the imaging trajectory.

* * * * *